United States Patent
Cuskaden et al.

(10) Patent No.: US 6,749,536 B1
(45) Date of Patent: Jun. 15, 2004

(54) EXERCISING USING A PUBLIC COMMUNICATION NETWORK

(75) Inventors: Sandy M. Cuskaden, Foster City, CA (US); Arvid G. Evans, Suisun City, CA (US)

(73) Assignee: Sprint Communications Company, L.P., Overland Park, KS (US)

( * ) Notice: Subject to any disclaimer, the term of this patent is extended or adjusted under 35 U.S.C. 154(b) by 441 days.

(21) Appl. No.: 09/848,712

(22) Filed: May 3, 2001

(51) Int. Cl.⁷ .............................................. A63B 21/00
(52) U.S. Cl. ................. 482/1; 482/8; 482/900
(58) Field of Search ........................ 482/1–9, 900–902

(56) References Cited

U.S. PATENT DOCUMENTS

| | | | | |
|---|---|---|---|---|
| 5,466,200 A | * | 11/1995 | Ulrich et al. | 482/4 |
| 5,890,995 A | * | 4/1999 | Bobick et al. | 482/4 |
| 6,458,060 B1 | * | 10/2002 | Watterson et al. | 482/54 |

* cited by examiner

*Primary Examiner*—Glenn E. Richman (57) ABSTRACT

A communication interface is coupled to an exercise machine and the public communication network. The communication interface receives first exercise information from an exercise machine wherein the first exercise information indicates exercise performance. Some examples of exercise information are video and audio files for competitive tracking with voice and video interaction. The communication interface then generates first communication information based on the first exercise information. In one embodiment, the communication information is in Internet Protocol packets. The communication interface then transmits the first communication information over the public communication network. The communication interface then receives second communication information from the public communication network. The communication interface then generates second exercise information based on the second communication information wherein the second exercise information indicates a response to the exercise performance. The communication interface then transmits the second exercise information to the exercise machine.

10 Claims, 8 Drawing Sheets

EXERCISING USING A PUBLIC COMMUNICATION NETWORK

RELATED APPLICATIONS

Not applicable

FEDERALLY SPONSORED RESEARCH OR DEVELOPMENT

Not applicable

MICROFICHE APPENDIX

Not applicable

BACKGROUND OF THE INVENTION

1. Field of the Invention

The invention is related to the field of exercise systems and communication systems, and in particular, to an exercise system that communicates over a public communication network.

2. Description of the Prior Art

Exercise has increasingly become a higher priority in people's lives in order to improve one's health. In response, fitness centers and health clubs have emerged across the United States. In addition, different types of exercise equipment such as stairmasters and rowing machines have been developed to not only provide physical exertion but also to provide entertainment and information for the exerciser.

Some exercise equipment include audio and video components to provide friendlier user interfaces. Speakers and video displays encourage exercisers in simulated competition, which could be either computer generated or against another competitor. One prior system includes two competing rowing machines next to each other and connected via a communication link. A video screen on each rowing machine displays two rowing figures. Unfortunately, this exercise equipment is geographically limited to being next to each other or in the same room. Thus, in order for two competitors to interact on the exercise equipment, the two competitors must be proximately situated.

With entertainment games, users do not have to be proximately situated in order to compete. Users in various games communicate over public networks such as the Internet and public switched telephone network (PSTN). One example is on-line gaming where users gamble over the Internet. Other video game systems such as the Playstation 2™ include network peripherals so people can play video games against each other over a communication network.

In the health care industry, certain medical devices are also connected to communication networks. Therefore, remote measurements, such as blood pressure, can then be made over the communication networks. Various appliances are also being connected to communication networks. One integrated circuit can be used in various appliances to be connected to the Internet/Ethernet. This integrated circuit named the "System on a Chip" (SOC) by Rabbit Semiconductor of Davis, Calif. includes multiple serial ports, parallel ports, flash memory, RAM, EEPROM, an Ethernet interface, an IP stack, and a 30 MHz 16-bit microprocessor.

Unfortunately, none of the prior systems allows users to exercise together or against each other that are situated remotely from each other.

SUMMARY OF THE INVENTION

The invention solves the above problems by exercising using a public communication network. A communication interface is coupled to an exercise machine and the public communication network. The communication interface receives first exercise information from an exercise machine wherein the first exercise information indicates exercise performance. Some examples of exercise information are video and audio files for competitive tracking with voice and video interaction, telemetry data related to performance monitoring, and body conditions such as blood pressure and heart rate.

The communication interface then generates first communication information based on the first exercise information. In one embodiment, the communication information is in Internet protocol (IP) packets. The communication interface then transmits the first communication information over the public communication network. The communication interface receives second communication information from the public communication network. The communication interface then generates second exercise information based on the second communication information wherein the second exercise information indicates a response to the exercise performance. The communication interface then transmits the second exercise information to the exercise machine.

In one embodiment, an exercise server receives the first communication information from the public communication network. The exercise server determines a response to the exercise performance based on the first communication information. The exercise server then generates the second communication information based on the response of the exercise performance. The exercise server transmits the second communication information from the exercise server to the public communication network.

The invention allows exercisers to advantageously interact in geographically diverse locations. This interaction provides competition or camaraderie so exercisers do not have to exercise alone. For example, some people prefer personal trainers to help with techniques and provide motivation. With this system, an exerciser can benefit from a personal trainer who is not in the same location. Thus, the exercising becomes more entertaining. In addition, this combination allows exercise enthusiasts to form groups with similar interests and energy.

Also, the invention advantageously allows the exerciser to interact with more powerful systems that store performance data, track competitions, and save physical measurements of body conditions. In some embodiments, when emergency situations arise, an alarm system can be notified to prevent injury or serious illness.

A particular reference number in one figure refers to the same element in all of the other figures.

DETAILED DESCRIPTION OF THE INVENTION

Figure 1:
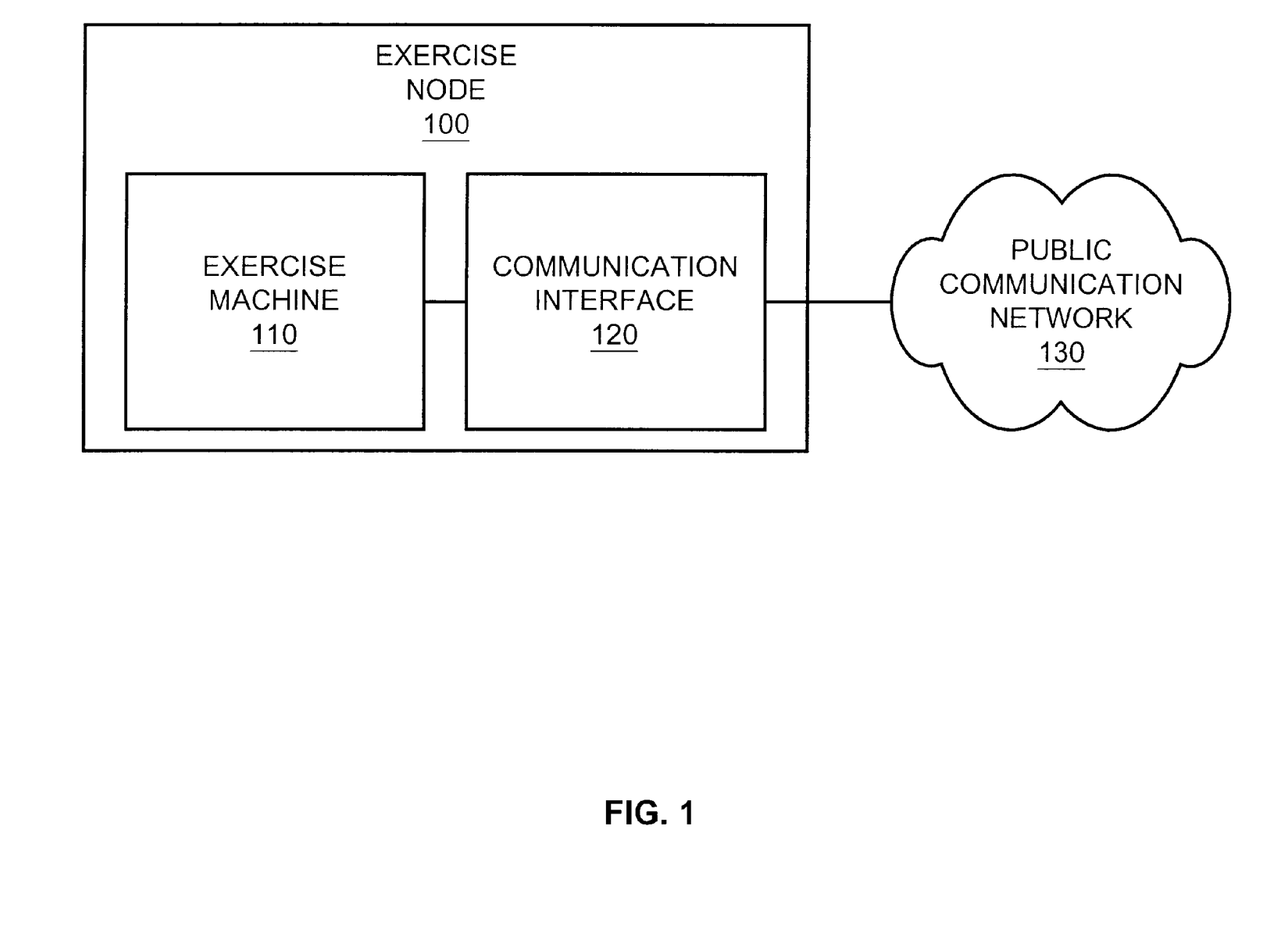
FIG. 1 is a system level block diagram of an example of the invention.
Figure 2:
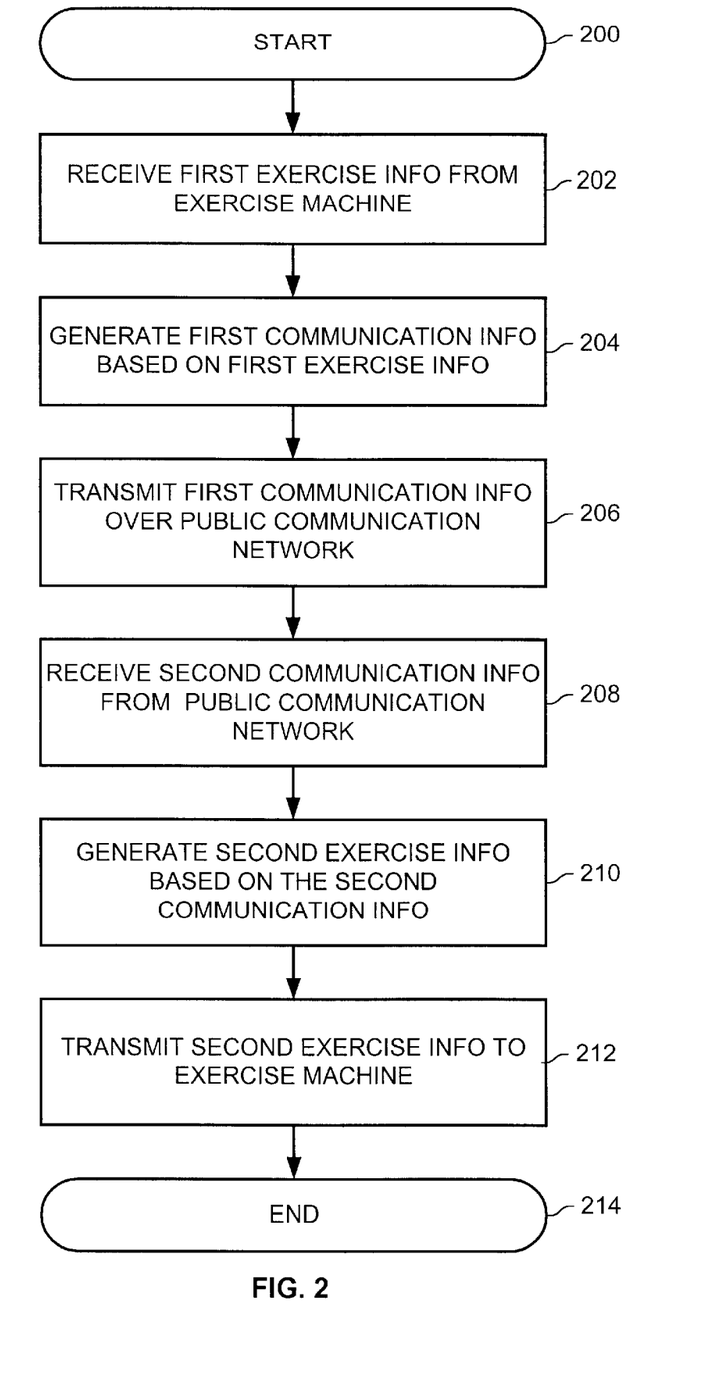
FIG. 2 is a flow chart of a communication interface in an example of the invention.

Exercise Node With Public Communication Network—FIGS. 1–2

FIG. 1 depicts a system level block diagram of an example of the invention. An exercise node 100 is comprised an exercise machine 110 and a communication interface 120. The exercise machine 110 is connected to the communication interface 120. The communication interface 120 is connected to a public communication network 130. In other embodiments, the connections between the components in FIGS. 1, 3, 6, and 8 are wireless connections to provide further geographic flexibility or increased rates of transmission.

The exercise machine 110 is any conventional exercise machine configured to transmit first exercise information to the communication interface 120 and receive second exercise information from the communication interface 120. Some examples of the exercise machine are stairmasters, bicycles, rowing machines, and scrolling climbing walls.

Exercise information is any information, data, or file that relates to the exercise performed on the exercise machine 110. The exercise information could be in any audio, video, data, or combination of audio, video, and data format. Some examples of exercise information are video and audio files for competitive tracking with voice and video interaction, telemetry data related to performance monitoring, and physical measurements of body conditions such as blood pressure and heart rate. Exercise is any activity that requires physical exertion, which improves health and fitness. Exercise typically provides a cardiovascular workout, strength training, or the combination of both.

The communication interface 120 is an interface between the exercise machine 110 and the public communication network 130 that is configured to (1) receive first exercise information from the exercise machine 110, (2) generate first communication information based on the first exercise information, (3) transmit the first communication information over the public communication network 130, (4) receive second communication information from the public communication network 130, (5) generate second exercise information based on the second communication information, and (6) transmit the second exercise information to the exercise machine 110. In some embodiments, the communication interface 120 is included within the exercise machine 110.

The communication information is any information, data, or file related to the exercise information in a format for transmission over the public communication network 130. The communication information could be in any audio, video, data, or combination of audio, video, and data format that is suitable for transmission over the public communication network 130. The public communication network 130 is any network of communication devices that provides communication services to the general public. Some examples are the Internet and the public switched telephone network.

In operation, the exercise machine 110 transmits the first exercise information to the communication interface 120. FIG. 2 depicts a flow chart of the communication interface 120 in an example of the invention. FIG. 2 begins in step 200. In step 202, the communication interface 120 receives the first exercise information wherein the first exercise information indicates exercise performance. In step 204, the communication interface 120 generates the first communication information based on the first exercise information.

In step 206, the communication interface 120 transmits the first communication information over the public communication network 130. In some embodiments, the destination of the first communication information is another exercise node connected to the public communication network 130. In other embodiments, the destination is an exercise application server connected to the public communication network. This exercise application server may use a computer-generated simulation or may exchange communication information with other exercise nodes to provide a simulation to groups of participants. One example of the exercise application server is discussed below in FIG. 7.

In step 208, the communication interface 120 receives the second communication information from the public communication network 130. In step 210, the communication interface 120 generates second exercise information based on the second communication information wherein the second exercise information indicates a response to the exercise performance. A response to the exercise performance is any information, data, or file generated in reply to the exercise activity performed on the exercise machine 110. Some examples of a response are data from a computer-generated simulation and information from another competing exercise node. In step 212, the communication interface 120 transmits the second exercise information to the exercise machine 110. FIG. 2 ends in step 214.

This combination of the exercise machine 110, the communication interface 120, and the public communication network 130 allows exercisers to advantageously interact in geographically diverse locations. This interaction provides competition or camaraderie so exercisers do not have to exercise alone. For example, some people prefer personal trainers to help with techniques and provide motivation. With this system, an exerciser benefit from a personal trainer who is not in the same location. Thus, the exercising becomes more entertaining. In addition, this combination allows exercise enthusiasts to form groups with similar interests and energy.

Also, the combination advantageously allows the exerciser to interact with more powerful systems that store performance data, track competitions, and save physical measurements of body conditions. In some embodiments, when emergency situations arise, an alarm system can be notified to prevent injury or serious illness.

Exercise Node With SOC Device and Public Communication Network—FIGS. 3–8

FIGS. 3–8 disclose embodiments of the invention, but the invention is not restricted to the configuration provided below. Those skilled in the art will appreciate numerous variations in exercise and communication system configuration and operation that are within the scope of the invention. Those skilled in the art will also appreciate how the principles illustrated in this example can be used in other examples of the invention.

Figure 3:
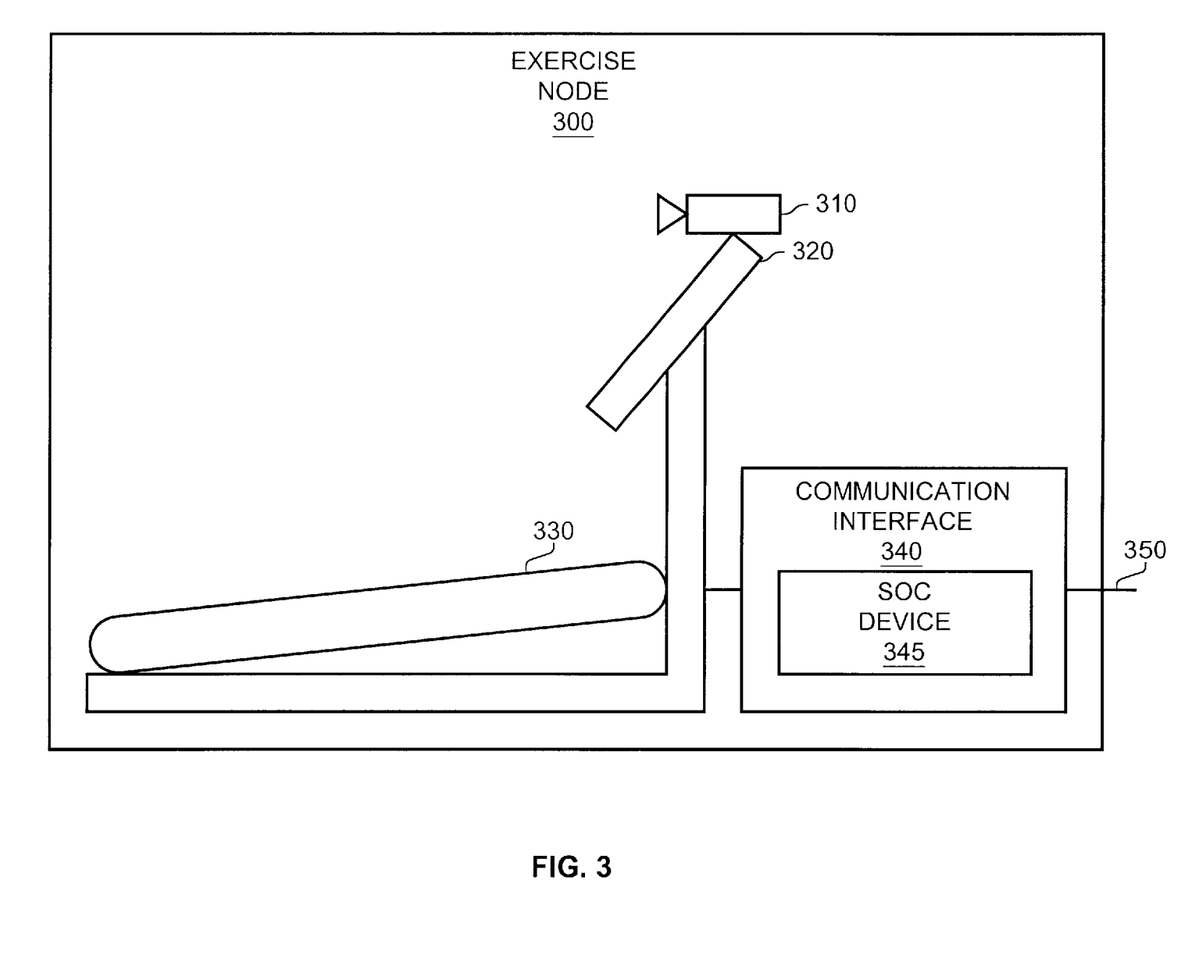
FIG. 3 is a block diagram of an exercise node in an example of the invention.

FIG. 3 depicts a block diagram of an exercise node 300 in an example of the invention. The exercise node 300 comprises a video camera 310, a control and display 320, a treadmill 330, a communication interface 340, and a public communications link 350. The video camera 310 is connected to the control and display 320. The control and display 320 are connected to the treadmill 330. The treadmill 330 is connected the communication interface 340. The communication interface 340 includes a "System on a Chip" (SOC) device 345. The communication interface 340 is connected to the public communications link 350. In one embodiment in FIG. 6, the public communications link 350 is connected to the Internet 660 and a modem 620, which is connected to the public switched telephone network 630. In another embodiment in FIG. 8, the public communications link 350 is connected to the Internet 860.

The video camera 310 is a conventional video camera such as a web camera. The control and display 320 is a combination of a conventional control panel for the treadmill 330 and a video display for displaying a video image of a competing exerciser.

The SOC device 345 is from Rabbit Semiconductor of Davis, Calif. The SOC device 345 includes various components needed for an apparatus to be connected to the Internet or an Ethernet. In one embodiment, the SOC device 345 includes multiple serial ports, parallel ports, flash memory, RAM, EEPROM, and a 30 MHz 16-bit microprocessor. In other embodiments, the SOC device 345 may also include an Ethernet interface and an IP stack.

Figure 4:
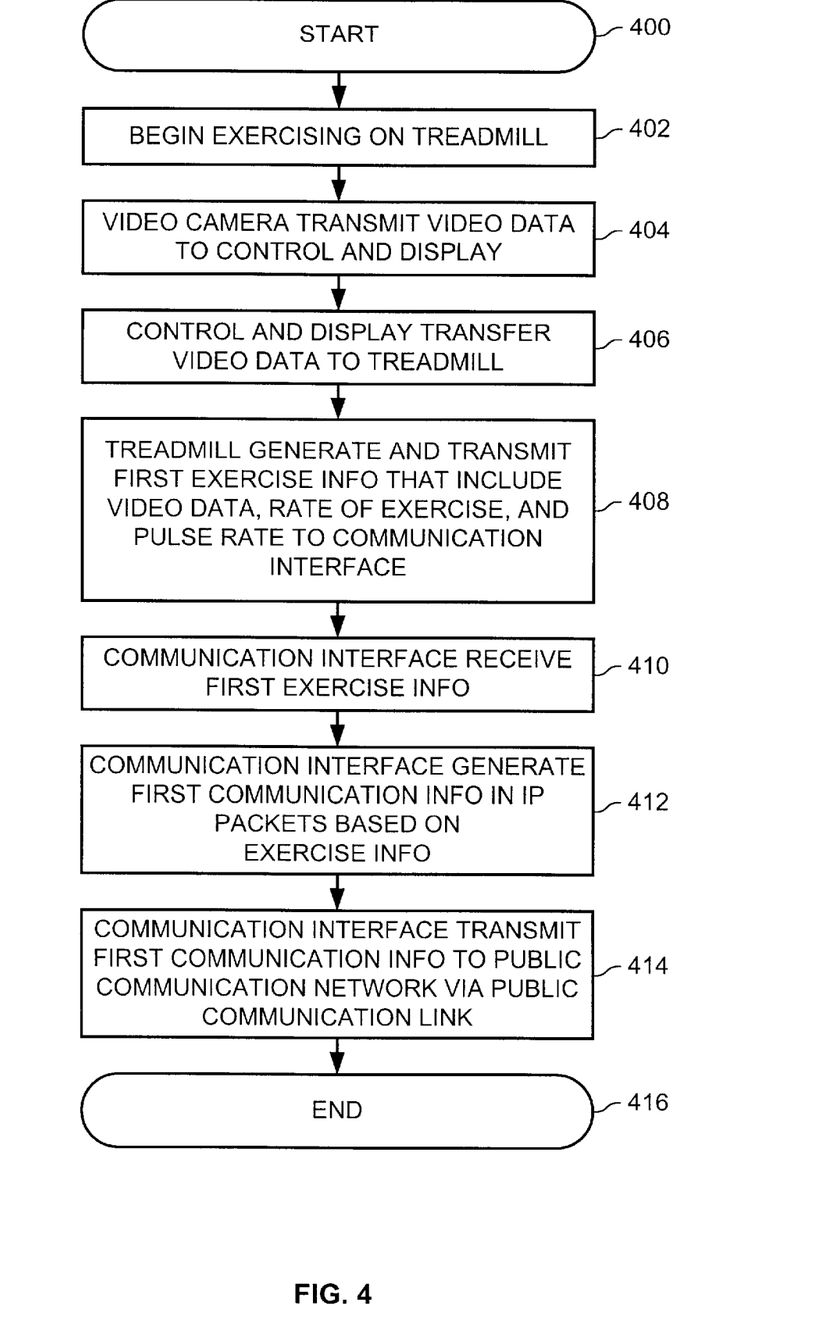
FIG. 4 is a flow chart for transmitting from an exercise node in an example of the invention.

FIG. 4 depicts a flow chart for transmitting from the exercise node 300 in an example of the invention. FIG. 4 begins in step 400. In step 402, the exerciser begins exercising on the treadmill 330. In step 404, the video camera 310 transmits video data to the control and display 320. In step 406, the control and display 320 transfers video data to the treadmill 330. In step 408, the treadmill 330 generates and transmits the first exercise information that includes the video data from the video camera, a rate of exercise such as miles per hour, and a pulse rate to the communication interface 340. Some examples of other rates of exercise are stairs per time, pounds per time, and rows per time. In other embodiments, the exercise information may include any physical measurements for tracking individual body conditions. Some conventional treadmills typically keep track of the rate of exercise and the pulse rate.

In step 410, the communication interface 340 receives the first exercise information. The communication interface 340 then generates first communication information based on the first exercise information in step 412. Those skilled in the art will understand there are numerous types of formats the communication information may be in. For this embodiment, the first communication information is in IP packet format. In step 414, the communication interface 340 transmits the first communication information to a public communication network via the public communication link 350. The destination of the first communication information and origination of the second communication information could be an exercise application server or to another exercise node as discussed below in FIGS. 6 and 8. FIG. 4 ends in step 416.

Figure 5:
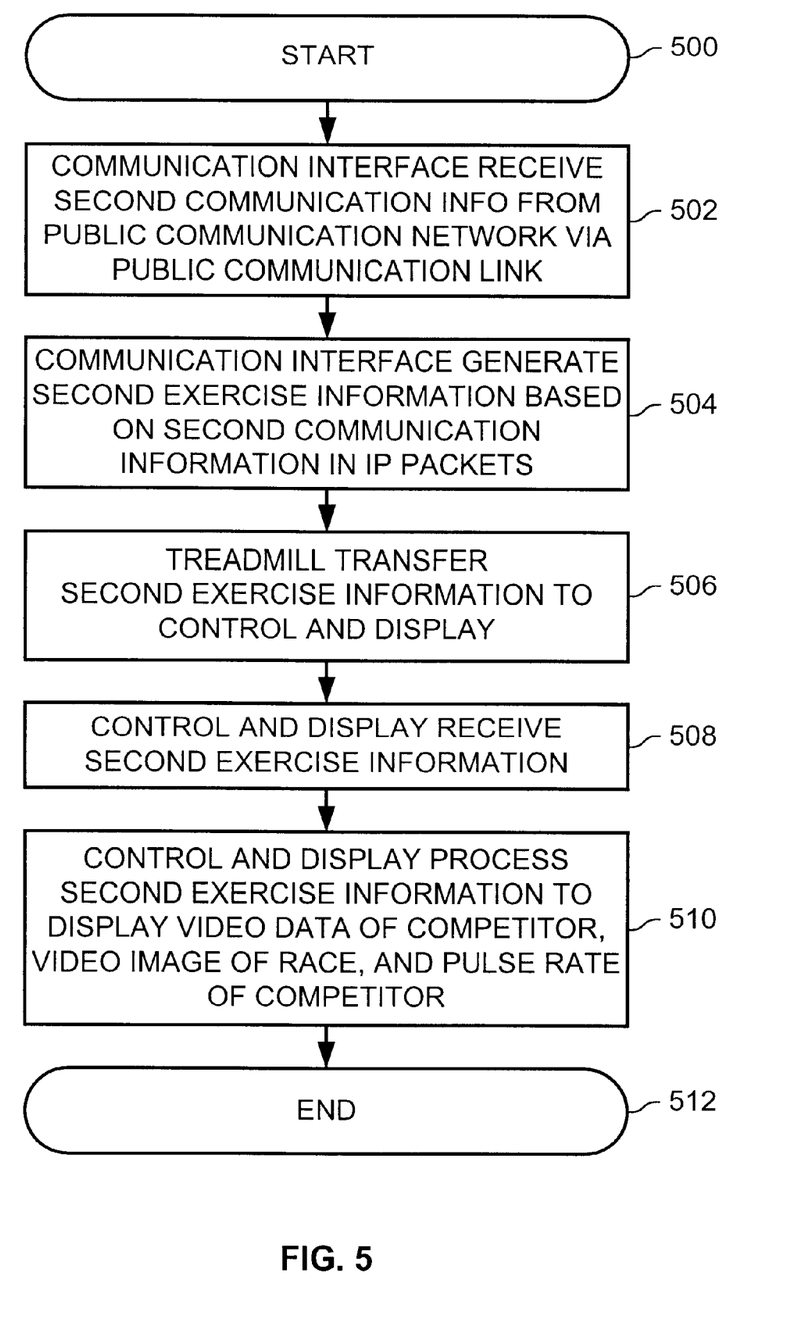
FIG. 5 is a flow chart for receiving into an exercise node in an example of the invention

FIG. 5 depicts a flow chart for receiving into the exercise node 300 in an example of the invention. FIG. 5 begins in step 500. In step 502, the communication interface 340 receives second communication information from the public communication network via the public communication link 350. The communication interface 340 then generates second exercise information based on the second communication information, which is in IP packet format. In step 506, the treadmill 330 transfers the second exercise information to the control and display 320. In step 508, the control and display 320 then receives the second exercise information. In step 510, the control and display 320 processes the second exercise information to display the video data of the competitor, show a computer image of the exerciser and the competitor in a race which simulates various running terrain, and display the pulse rate of both the exerciser and the competitor. In another embodiment, the second exercise information includes pre-stored exercise training or scripts. FIG. 5 ends in step 512.

Figure 6:
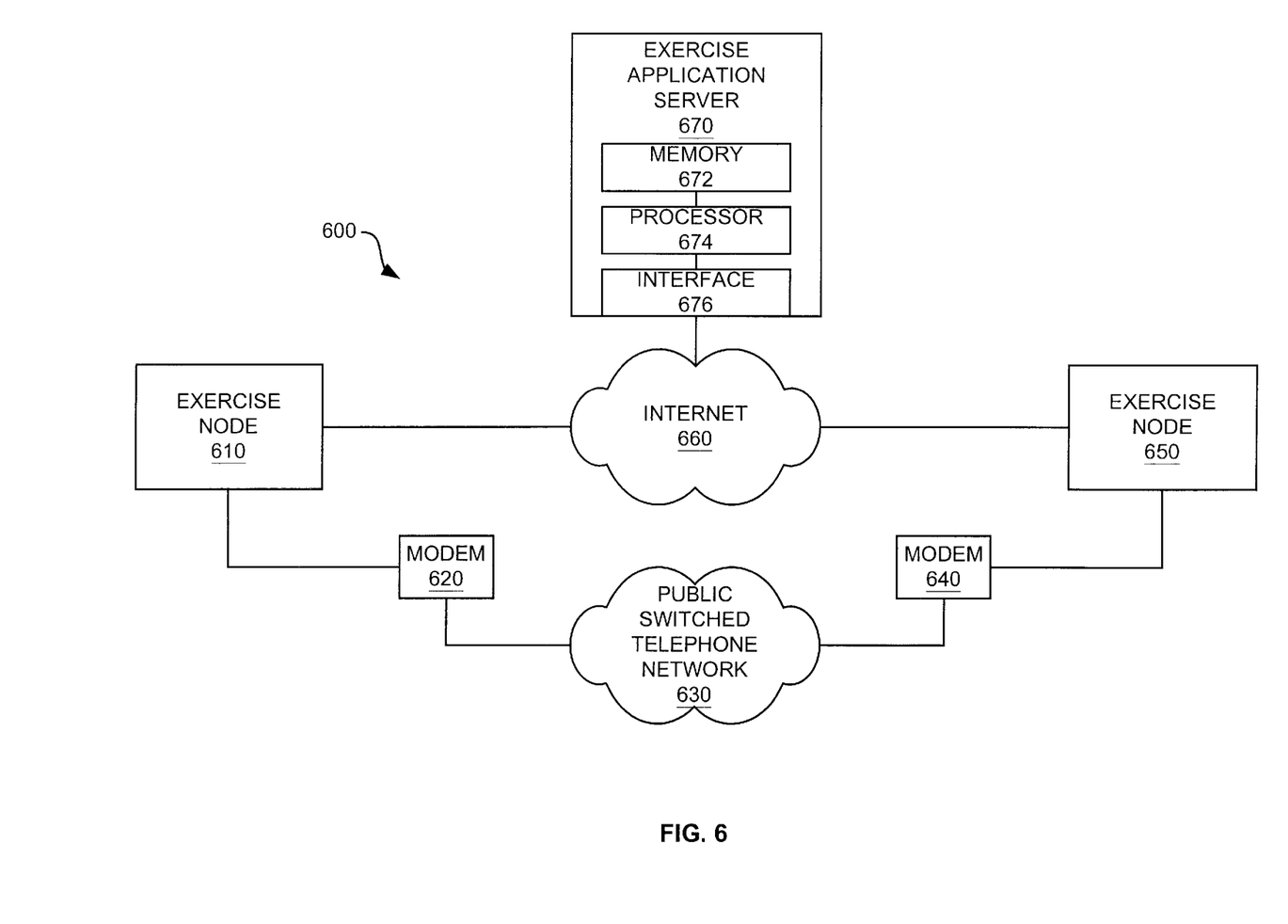
FIG. 6 is a block diagram of a peer-to-peer network in an example of the invention.

FIG. 6 is a block diagram of a peer-to-peer network 600 in an example of the invention. The peer-to-peer network 600 includes an exercise node 610, a modem 620, a public switched telephone network (PSTN) 630, a modem 640, an exercise node 650, the Internet 660, and an exercise application server 670. The exercise application server 670 comprises a memory 672, a processor 674, and an interface 676. The exercise node 610 is connected to the modem 620 and the Internet 660. The modem 620 is connected to the PSTN 630. The PSTN 630 is connected to the modem 640. The modem 640 is connected to the exercise node 650. The exercise node 650 is connected to the Internet 660. The Internet 660 is connected to the exercise application server 670.

In one embodiment for a peer-to-peer communication, the exercise node 610 communicates with the exercise node 650 via the modem 620, the PSTN 630, and the modem 640. In some embodiments, the modem 620 may be included within the communication interface 340. The modem 620 is a conventional dial-up modem that communicates with the PSTN 630. In another embodiment for a peer-to-peer communication, the exercise node 610 communicates with the exercise node 650 via the Internet 660.

The exercise application server 670 includes conventional components of a server with the memory 672, the processor 674, and the interface 676. The processor 674 executes instructions or software stored in the memory 672. The processor 674 also uses the memory for temporary and permanent storage for data. The processor 674 exchanges data with the Internet 660 via the interface 676. The operation of the exercise application server 670 is discussed below in FIG. 7.

Figure 7:
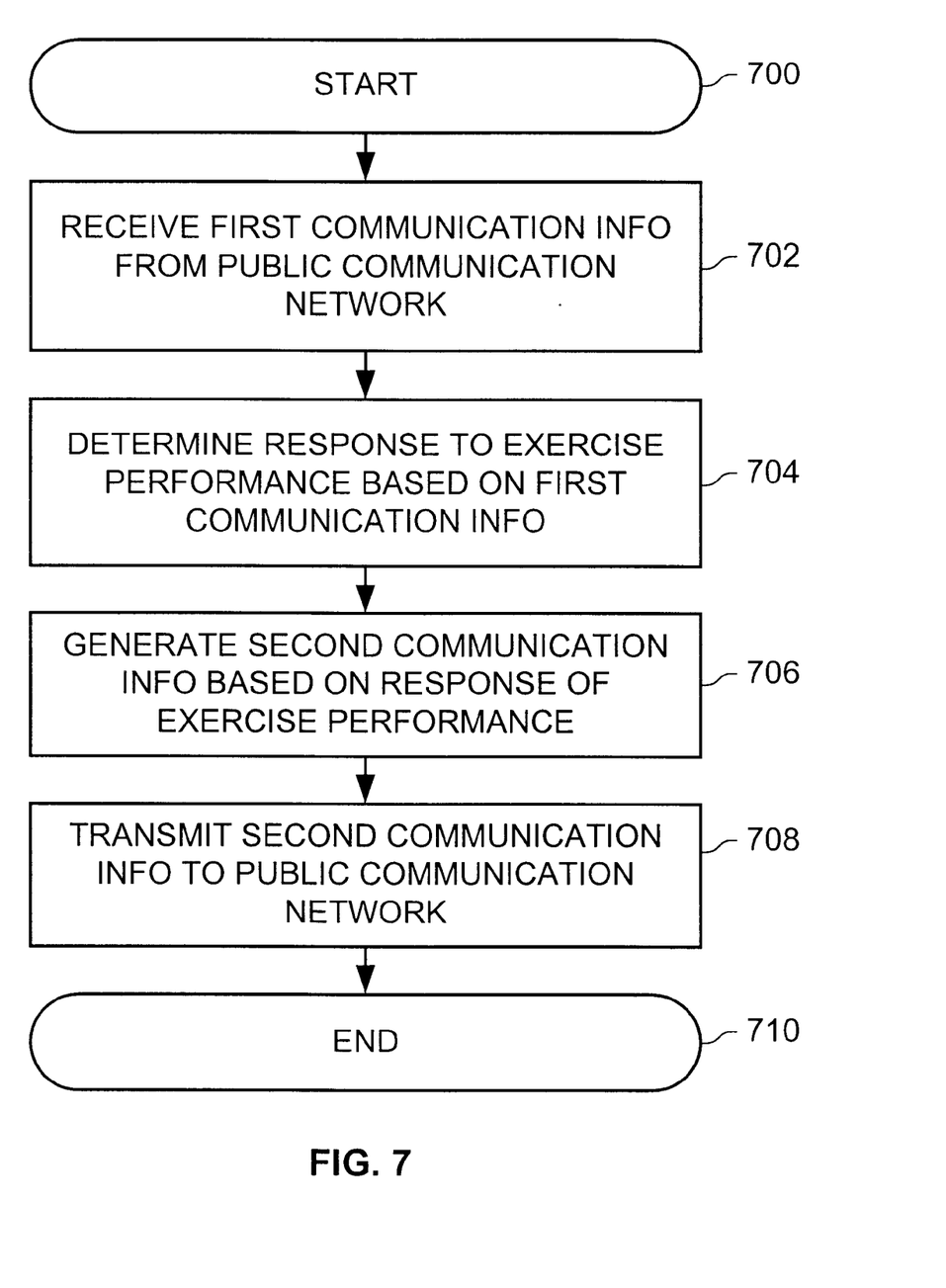
FIG. 7 is a flow chart of an exercise application server in an example of the invention.

FIG. 7 depicts a flow chart of the exercise application server 670 in an example of the invention. FIG. 7 begins in step 700. In this embodiment for a peer-to-peer communication, two competitors interact with each other by communicating with the exercise application server 670 separately. In step 702, the exercise application server 670 receives the first communication information from the Internet 660. In step 704, the exercise application server 670 then determines a response to the exercise performance based on the first communication information. A response to the exercise performance is any information, data, or file generated in reply to the exercise activity performed on the exercise machine 110. Some examples of a response are data from a computer-generated simulation and information from another competing exercise node.

In this embodiment, the exercise application server 670 creates a computer-generated simulation of a race with two exercisers at separate exercise nodes. In one scenario, an exerciser may communicate with the exercise application server 670 to exercise with another competitor. However, if no competitor is available, the exerciser competes with the exercise application server 670 in a computer generated simulation.

In another embodiment, the exercise application server 670 performs authentication and authorization for exercisers. The exercise application server 670 may also execute exercise applications that simulate competitions or tasks. These exercise application may also control the exercise machine. For example, the exercise application server 670 lowers the runner's exercise level if the body conditions indicate the runner is exercising too strenuously. Also, the exercise application server 670 collects and stores the communication information including performance statistics, competitive tracking, and health statistics.

In another embodiment, the exercise application server 670 monitors medical data. When the medical data indicates overstress or an impending medical situation, the exercise application server 670 generates and transmits an emergency message to an alarm system to properly handle the situation. This functionality may also be implemented in the communication interface 340.

In step 706, the exercise application server 670 generates the second communication information based on the response of the exercise performance. In step 708, the exercise application server 670 transmits the second communication information to the Internet. FIG. 7 ends in step 710.

Figure 8:
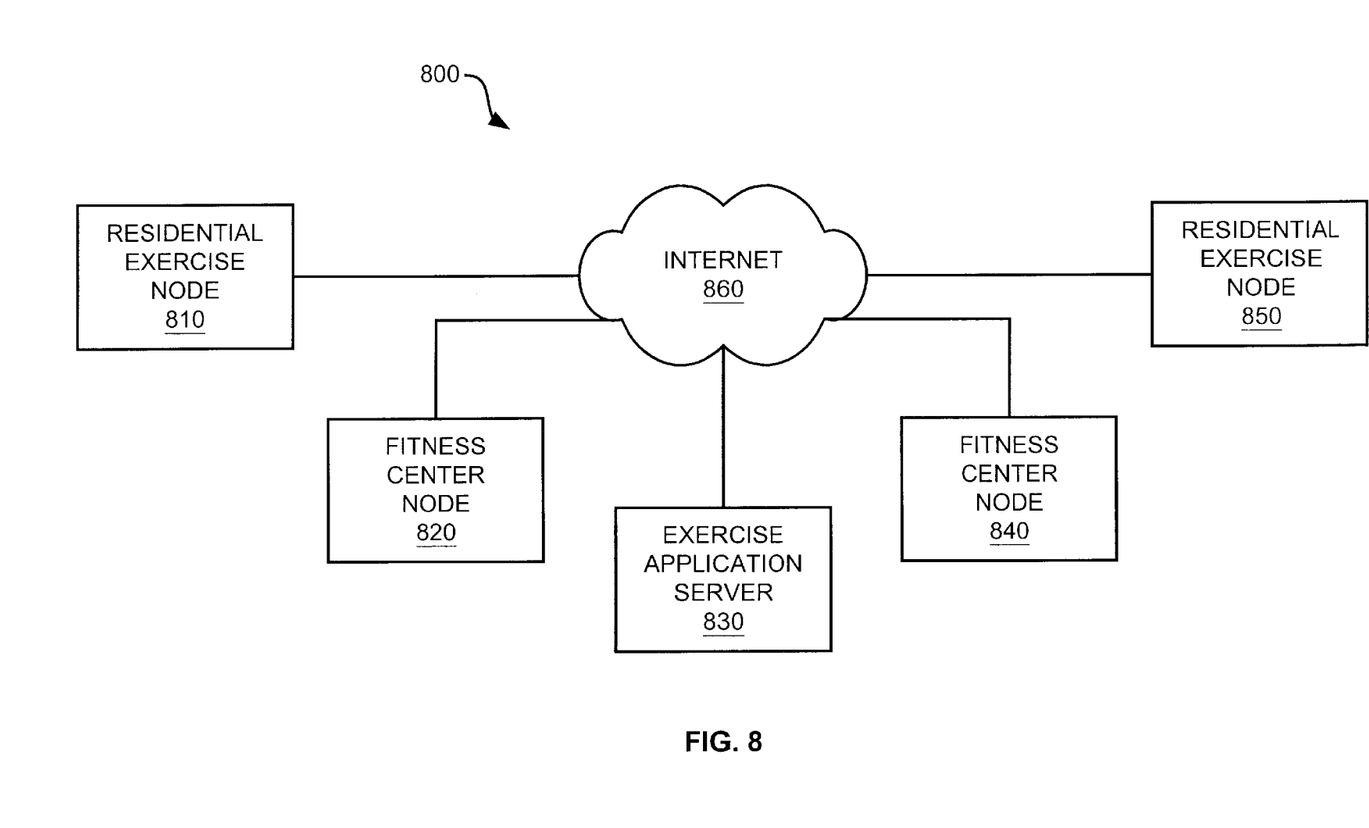
FIG. 8 is a block diagram of a multi-point network in an example of the invention.

FIG. 8 is a block diagram of a multi-point network 800 in an example of the invention. The multi-point network 800 includes a residential exercise node 810, a fitness center node 820, an exercise application server 830, a fitness center node 840, a residential exercise node 850, and the Internet 860. The Internet 860 is connected to the residential exercise node 810, the fitness center node 820, the exercise application server 830, the fitness center node 840, and the residential exercise node 850.

The fitness center node 820 and the fitness center node 840 are a group of the exercise nodes 300 as discussed in FIG. 3. In some embodiments, the communication interface 340 may interconnect multiple exercise machines. The residential exercise node 810, the fitness center node 820, the fitness center node 840, and the residential exercise node 850 can communicate with each other via the Internet 860 directly or through the exercise application server 830 as discussed above in FIG. 6. FIG. 8 illustrates how multiple exercisers can compete in large communication network. In one scenario, two friends compete in a rowing match, while one is at home and the other is at the fitness center.

The above-described elements can be comprised of instructions that are stored on storage media. The instructions can be retrieved and executed by a processor. Some examples of instructions are software, program code, and firmware. Some examples of storage media are memory devices, tape, disks, integrated circuits, and servers. The instructions are operational when executed by the processor to direct the processor to operate in accord with the invention. Those skilled in the art are familiar with instructions, processor, and storage media.

Those skilled in the art will appreciate variations of the above-described embodiments that fall within the scope of the invention. As a result, the invention is not limited to the specific examples and illustrations discussed above, but only by the following claims and their equivalents.

We claim:

1. A method of exercising using a public communication network, the method comprising:

receiving first exercise information into a communication interface from an exercise machine coupled to the communication interface wherein the first exercise information indicates exercise performance;

in the communication interface, generating first communication information based on the first exercise information;

transmitting the first communication information from the communication interface over the public communication network;

receiving second communication information into the communication interface from the public communication network;

in the communication interface, generating second exercise information based on the second communication information wherein the second exercise information indicates a response to the exercise performance; and transmitting the second exercise information from the communication interface to the exercise machine.

2. The method of claim 1 wherein the first exercise information comprises audio data.

3. The method of claim 1 wherein the first exercise information comprises video data.

4. The method of claim 1 wherein the first exercise information comprises data indicating a body condition of an exerciser.

5. The method of claim 1 wherein the first communication information comprises audio data.

6. The method of claim 1 wherein the first communication information comprises video data.

7. The method of claim 1 wherein the first communication information comprises data indicating a body condition of an exerciser.

8. The method of claim 1 wherein the public communication network comprises the Internet.

9. The method of claim 1 wherein the public communication network comprises a public switched telephone network.

10. The method of claim 1 further comprising:

receiving the first communication information into an exercise server from the public communication network;

in the exercise server, determining the response to the exercise performance based on the first communication information;

in the exercise, server, generating the second communication information based on the response to the exercise performance; and transmitting the second communication information from the exercise server to the public communication network.

\* \* \* \* \*